United States Patent
Buelow et al.

(10) Patent No.: US 10,297,089 B2
(45) Date of Patent: May 21, 2019

(54) VISUALIZING VOLUMETRIC IMAGE OF ANATOMICAL STRUCTURE

(71) Applicant: KONINKLIJKE PHILIPS N.V., Eindhoven (NL)

(72) Inventors: Thomas Buelow, Grosshansdorf (DE); Daniel Bystrov, Hamburg (DE); Rafael Wiemker, Kisdorf (DE); Dominik Benjamin Kutra, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/513,184

(22) PCT Filed: Sep. 18, 2015

(86) PCT No.: PCT/EP2015/071464
§ 371 (c)(1),
(2) Date: Mar. 22, 2017

(87) PCT Pub. No.: WO2016/046083
PCT Pub. Date: Mar. 31, 2016

(65) Prior Publication Data
US 2018/0025546 A1    Jan. 25, 2018

(30) Foreign Application Priority Data
Sep. 24, 2014    (EP) .................................... 14186109

(51) Int. Cl.
G06F 19/00    (2018.01)
G06T 19/00    (2011.01)
G06T 19/20    (2011.01)

(52) U.S. Cl.
CPC .............. *G06T 19/20* (2013.01); *G06T 19/00* (2013.01); *G06T 19/003* (2013.01); *G06F 19/321* (2013.01); *G06T 2219/008* (2013.01)

(58) Field of Classification Search
None
See application file for complete search history.

(56) References Cited

U.S. PATENT DOCUMENTS 8,675,022 B2    3/2014    Liang et al.
8,736,609 B2    5/2014    Brabec
(Continued)

OTHER PUBLICATIONS

"IRIS 2000 User Manual", Jun. 17, 2007.

*Primary Examiner* — Frank S Chen

(57) ABSTRACT

A system and method is provided for visualizing a volumetric image of an anatomical structure. Using a first view of the volumetric image showing a non-orthogonal cross-section of a surface of the anatomical structure, a local orientation of the surface within the volumetric image is determined, namely by analyzing the image data of the volumetric image. Having determined the local orientation of the surface, a second view is generated of the volumetric image, the second view being geometrically defined by a viewing plane intersecting the surface of the anatomical structure in the volumetric image orthogonally. Accordingly, the surface is shown in a sharper manner in the second view than would typically be the case in the first view. Advantageously, the user can manually define or correct a delineation of the outline of the anatomical structure in a more precise manner. Moreover, various other advantageously uses of such a second view exist, such as facilitating the image interpretation by the clinician, more reliable further automatic analysis, etc.

14 Claims, 4 Drawing Sheets

(56) References Cited

U.S. PATENT DOCUMENTS

| | | | |
|---|---|---|---|
| 2002/0184470 A1 | 12/2002 | Weese et al. | |
| 2003/0011619 A1* | 1/2003 | Jacobs | G06T 15/80 345/619 |
| 2007/0291000 A1* | 12/2007 | Liang | G06F 3/04815 345/161 |
| 2011/0063325 A1* | 3/2011 | Saunders | G09G 5/00 345/639 |
| 2011/0206255 A1 | 8/2011 | Buelow | |
| 2012/0290976 A1* | 11/2012 | Lahm | G06T 19/00 715/810 |
| 2013/0021372 A1 | 1/2013 | Wiemker et al. | |

* cited by examiner

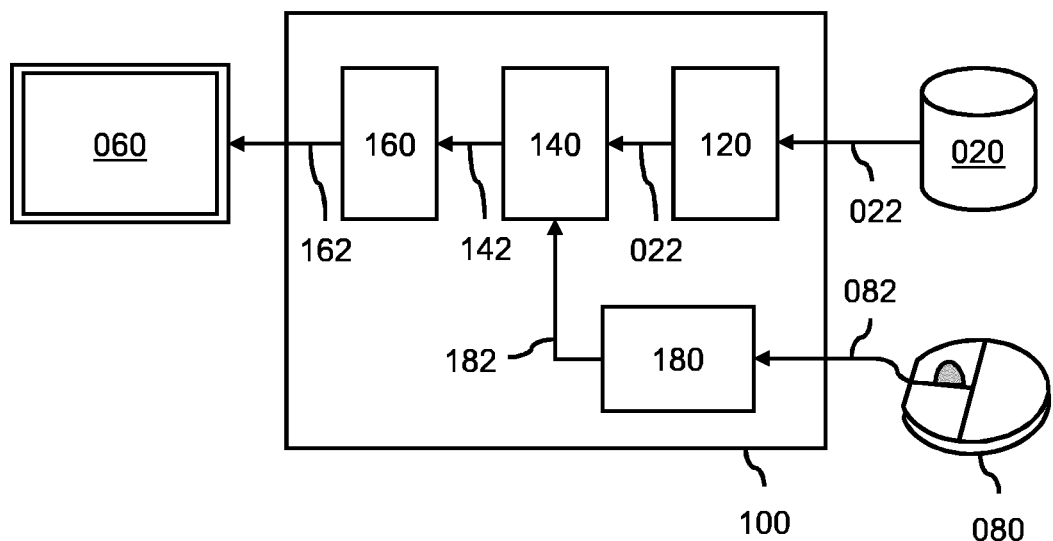
Fig. 1
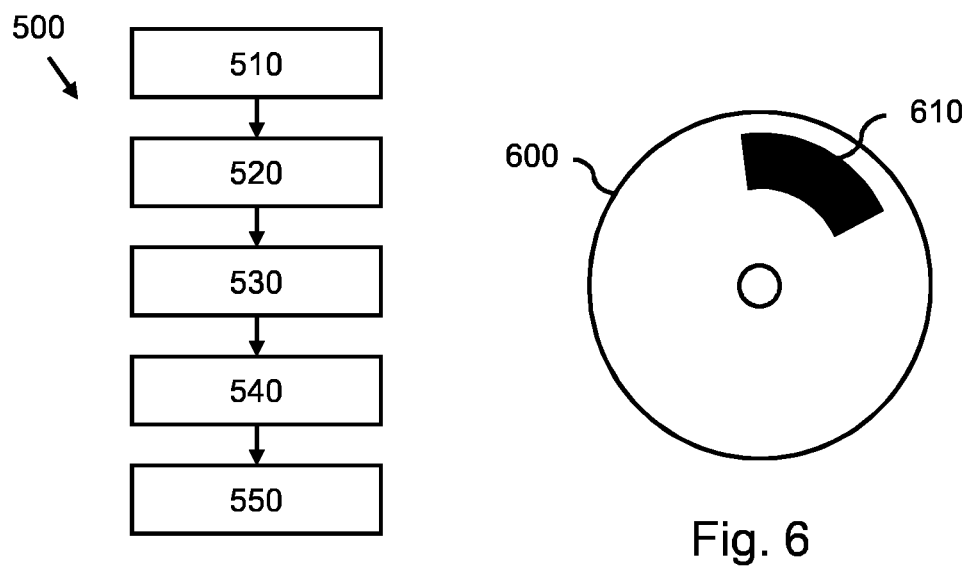
Fig. 5
Fig. 6

VISUALIZING VOLUMETRIC IMAGE OF ANATOMICAL STRUCTURE

CROSS-REFERENCE TO PRIOR APPLICATIONS

This application is the U.S. National Phase application under 35 U.S.C. § 371 of International Application No. PCT/EP2015/071464, filed on Sep. 18, 2015, which claims the benefit of European Patent Application No. 14186109.6, filed on Sep. 24, 2014. These applications are hereby incorporated by reference herein.

FIELD OF THE INVENTION

The invention relates to a system and method for visualizing a volumetric image of an anatomical structure. The invention further relates to a workstation and imaging apparatus comprising the system. The invention further relates to a computer program product comprising instructions for causing a processor system to perform the method.

BACKGROUND OF THE INVENTION

Volumetric images may be presented in various ways to a user. For example, if the volumetric image is represented by the image data of a stack of 2D image slices, one of the 2D image slices may be selected for display, or an oblique slice may be generated using a multi-planar reformatting technique. Another example is that if the volumetric image is represented by three-dimensional [3D] image data, a volume rendering technique may be used to generate a two-dimensional [2D] projection of the 3D image data.

In general, such presentations of a volumetric image are referred to as views of the volumetric image, and said generating of the views is referred to as view generation. Several of such techniques are known from the field of image processing. Here, the geometric arrangement of a view with respect to the volumetric image may be defined by a viewing plane intersecting the volumetric image. Such a viewing plane may represent, e.g., a geometry for multi-planar reformatting, an image slice selection, a projection plane, etc.

The volumetric image may show an anatomical structure such as an organ, a part of an organ, etc. It may be desirable for a clinician to obtain a view of the surface of the anatomical structure in the volumetric image, for example, to enable the clinician to manually define or correct a delineation of the outline of the anatomical structure in the view.

SUMMARY OF THE INVENTION

A problem of obtaining a view of the surface of the anatomical structure is that such a view frequently shows the surface in an unclear manner.

It would be advantageous to provide a system or method which obtains a view of the surface of the anatomical structure which shows the surface in a clearer manner.

To better address this concern, a first aspect of the invention provides a system for visualizing a volumetric image of an anatomical structure, the system comprising:
an image interface for accessing image data of the volumetric image;
a display processor configured for:
i) generating a first view of the volumetric image, the first view being geometrically defined by a first viewing plane intersecting the volumetric image, the first view showing a cross-section of a surface of the anatomical structure,
ii) determining at least one location on the surface based on a position of an onscreen pointer;
iii) determining a local orientation of the surface within the volumetric image by analyzing the image data of the volumetric image, the local orientation being determined for the at least one location on the surface shown in the first view, and
iv) based on the local orientation being determined for the at least one location on the surface, generating a second view of the volumetric image, the second view being geometrically defined by a second viewing plane intersecting the surface of the anatomical structure in the volumetric image substantially orthogonally at the at least one location on said surface; and
a display output for generating and outputting display data, the display data representing an output of the display processor.

In a further aspect of the invention, a workstation and imaging apparatus are provided comprising the system.

In a further aspect of the invention, a method is provided for visualizing a volumetric image of an anatomical structure, the method comprising:
accessing image data of the volumetric image;
generating a first view of the volumetric image, the first view being geometrically defined by a first viewing plane intersecting the volumetric image, the first view showing a cross-section of a surface of the anatomical structure;
determining at least one location on the surface based on a position of an onscreen pointer and a local orientation of the surface within the volumetric image by analyzing the image data of the volumetric image, the local orientation being determined for the at least one location on the surface shown in the first view;
based on the local orientation being determined for the at least one location on the surface, generating a second view of the volumetric image, the second view being geometrically defined by a second viewing plane intersecting the surface of the anatomical structure in the volumetric image substantially orthogonally at the at least one location on said surface; and
generating and outputting display data, the display data representing an output of the display processor.

In a further aspect of the invention, a computer program product is provided comprising instructions for causing a processor system to perform the method above.

The aforementioned measures involve accessing image data of a volumetric image. For example, 3D image data may be accessed, e.g., formatted as a 3D array of voxels, or the image data of a stack of 2D image slices, e.g., each formatted as a 2D array of voxels or pixels. A first view of the volumetric image is generated which shows a cross-section of a surface of the anatomical structure. Such a first view may be generated as part of the system sequentially generating different views of the image data to enable a user to navigate through the volumetric image. However, this is not a limitation, in that the first view may also be generated within a different context. The first view is geometrically defined by a first viewing plane which defines the geometric relation between the first view and the volumetric image. For example, the viewing plane may represent a projection plane, a geometry for multi-planar reformatting or indicate an image slice selection. As such, the first view may have been generated using a view generation technique such as multi-planar reformatting. However, this is not a limitation, in that the first view may also correspond to a sub-selection of the 3D image data, e.g., an axial, coronal or sagittal slice. It is noted that the functionality described in this paragraph is known per se from the field of volumetric image display.

Furthermore, a local orientation of the surface of the anatomical structure within the volumetric image is determined, namely by analyzing the image data of the volumetric image. Here, the phrasing 'orientation ( . . . ) within the volumetric image' refers to a three-dimensional orientation, e.g., as described by a vector, and the adjective 'local' refers to the orientation representing the orientation of the surface at least at the one location. This location is a location in the volumetric image which is also shown in the first view.

Moreover, a second view of the volumetric image is generated by the system. Like the first view, the second view is geometrically defined by a viewing plane intersecting the volumetric image, namely a second viewing plane. However, additionally, the second viewing plane intersects the volumetric image in such a manner that the surface of the anatomical structure is substantially orthogonally intersected at the at least one location on said surface. Here, the term 'substantially orthogonally' refers to an orthogonal intersection, or one within a limited range of the 90 degrees representing an orthogonal intersection, e.g., within +/−20 degrees, +/−10 degrees, and/or within +/−5 degrees. For determining the appropriate geometry of the second view, use is made of the previously determined local orientation of the surface at the at least one location on the surface. Like the first view, the second view may be generated in various ways, e.g., by multi-planar reformatting if the second view represents an oblique slice through the volumetric image, by obtaining a different sub-selection of the 3D image data than that of the first view, etc.

Furthermore, display data is generated representing an output of the display processor. For example, the display data may first show the first view and then the second view, or may show both views simultaneously, e.g., side by side or as an overlay.

The inventors have recognized that, in volumetric image display, it may frequently occur that a view shows a cross-section which intersects the surface of an anatomical structure in a shallow manner, e.g., in a manner which is not substantially orthogonal. Such views show the surface of the anatomical structure in a blurred manner. For example, if the surface represents an outline of the anatomical structure, the first view may show the anatomical surface having a blurred outline. A specific example is that an axial cross-section through a volumetric breast image at the bottom of the breast typically shows the skin surface being intersected in a shallow manner which leads to a blurred outline. Disadvantageously, it may be difficult for a user to delineate the skin surface in such a view.

The aforementioned measures have the effect that, starting from a first view which shows a cross-section of a surface of the anatomical structure, the user is presented with a second view which shows an orthogonal cross-section of the surface of the anatomical structure. An orthogonal cross-section yields a sharper depiction of a surface than a shallow cross-section. Accordingly, the surface is shown in a sharper manner in the second view than would typically be the case in the first view. Advantageously, the user can manually define or correct a delineation of the outline of the anatomical structure in a more precise manner. Moreover, various other advantageously uses of such a second view exist, such as facilitating the image interpretation by the clinician, more reliable further automatic analysis, etc.

Optionally, the system further comprises a user interaction subsystem for enabling a user to position an onscreen pointer over the first view, and the display processor is configured for determining the at least one location on the surface based on a position of the onscreen pointer. By providing a user interaction subsystem, the user can interact with the system. For example, the user interaction subsystem may comprise an input device interface connected to an input device such as a mouse, keyboard, touchscreen, etc. Accordingly, the user may provide user input by operating the input device. In particular, the user may position an onscreen pointer, such as a cursor, over the first view. The display output may be part of the user interaction subsystem, thereby enabling the system to provide visual feedback on the user input provided by the user. Such functionality may be used for various purposes, such as navigate through the volumetric image, image annotation or image delineation. An example of the latter is the manually defining or correcting of a delineation of the outline of the anatomical structure, e.g., by tracing the outline of the anatomical structure with the onscreen pointer. The display processor may determine the at least one location on the surface based on a position of the onscreen pointer, e.g., by using the position directly, by selecting a contour nearest to the position of the onscreen pointer, etc. Accordingly, the second view shows the surface of the anatomical structure being substantially orthogonally intersected at or nearby the position of the onscreen pointer. Advantageously, the user may select the location at which the surface of the anatomical structure is substantially orthogonally intersected, e.g., by clicking a mouse button or hovering over the location with the onscreen pointer, thereby causing the system to generate and display the second view.

Optionally, the user interaction subsystem is configured for enabling the user to delineate the surface of the anatomical structure in the second view. The second view is thus generated and displayed at least in part for the purpose of enabling the user to delineate the surface of the anatomical structure in the second view. Such delineation may take the form of the user tracing the outline of the anatomical structure with the onscreen pointer. Since the second view typically shows the surface in a sharper manner than would typically be the case in the first view, the second view is more suitable for such delineation. As such, the user can delineate the outline of the anatomical structure in a more precise manner.

Optionally, the display processor is configured for:
  determining a volume of interest in the volumetric image which includes the at least one location on the surface; and
  generating the second view based on the volume of interest.

By determining the volume of interest, the second view is generated from a specific subset of the image data which includes the at least one location on the surface. By generating the second view based on the volume of interest, it is avoided that all of the image data of the volumetric image needs to be processed in generating the second view. For example, the volume of interest may represent a projection volume from which the second view is generated by means of volumetric projection. Another example is that the volume of interest defines the image data to which multi-planar reformatting is applied. The second viewing plane may be used in generating the second view from the volume of interest, e.g., by acting as a projection plane or as a geometric target for the multi-planar reformatting. Advantageously, in case the second view is generated as a smaller insert or overlay over the first view, e.g., showing only a neighborhood of the at least one location on the surface, the volume of interest may be selected to correspond to the smaller second view.

Optionally, the volume of interest has a cubical or a spherical shape. Cubical or spherical shapes are well suited as shapes for the volume of interest. Alternatively, however, the volume of interest may have a more general shape. It is noted that the shape may be pre-defined, application specific, or may be used-defined. For example, in the case of an elongated anatomical structure such as a bone, an elongated box may be used as volume of interest such that a larger portion of the surface of the bone is shown in a clearer manner.

Optionally, the display processor is configured for generating the second view as an overlay over part of the first view. The second view thus does not fully replace the first view. This may avoid the user being confused by a sudden change in view, and/or the replacement of the first view interrupting the user's navigation through the volumetric image. Advantageously, the overlay may be a local overlay, e.g., showing only a neighborhood of the at least one location on the surface, thereby maintaining the first view as surround.

Optionally, the part of the first view being overlaid corresponds to the volume of interest. As such, the second view is overlaid over a part of the first view which corresponds thereto, e.g., by showing a similar part of the anatomical structure. This is a particularly advantageous visualization in that it is intuitively comprehensible by a user.

Optionally, the display processor is configured for blending the second view with the first view at a boundary of the volume of interest so as to establish a gradual transition between the overlay of the second view and the first view. Accordingly, discontinuous transitions may be avoided at the boundary of the volume of interest.

Optionally, the display processor is configured for establishing the local orientation of the surface within the volumetric image as an orientation vector pointing in a direction of the steepest change in image intensity from the at least one location on the surface of the anatomical structure. The local orientation of the surface at the at least one location on the surface is thus represented by a vector, e.g., a three-dimensional vector. The steepest change in image intensity is typically indicative of an orientation of a surface. Various image processing techniques are known for determining such a steepest change. For example, an image filter may be applied to the image data, such as a Hessian filter.

Optionally, the display processor is configured for determining the second viewing plane by rotating the first viewing plane so as to contain the orientation vector with a rotation transformation about a smallest absolute rotation angle. The first viewing plane may be rotated about various different axes so as to contain the orientation vector, thereby yielding a different view for each different rotation transformation axis. By rotating the first viewing plane with a rotation transformation that has the smallest absolute rotation angle, the angulation of the second view with respect to the first view is minimized. Advantageously, it is easier for the user to interpret the second view.

In accordance with the above, a system and method may be provided for visualizing a volumetric image of an anatomical structure. Using a first view of the volumetric image showing a non-orthogonal cross-section of a surface of the anatomical structure, a local orientation of the surface within the volumetric image may be determined, namely by analyzing the image data of the volumetric image. Having determined the local orientation of the surface, a second view may be generated of the volumetric image, the second view being geometrically defined by a viewing plane intersecting the surface of the anatomical structure in the volumetric image orthogonally. Accordingly, the surface may be shown in a sharper manner in the second view than would typically be the case in the first view. Advantageously, the user may manually define or correct a delineation of the outline of the anatomical structure in a more precise manner. Moreover, various other advantageously uses of such a second view may exist, such as facilitating the image interpretation by the clinician, more reliable further automatic analysis, etc.

It will be appreciated by those skilled in the art that two or more of the above-mentioned embodiments, implementations, and/or aspects of the invention may be combined in any way deemed useful.

Modifications and variations of the workstation, the imaging apparatus, method and/or the computer program product, which correspond to the described modifications and variations of the system, can be carried out by a person skilled in the art on the basis of the present description.

A person skilled in the art will appreciate that the method may be applied to multi-dimensional image data, e.g. three-dimensional (3-D) or four-dimensional (4-D) images. A dimension of the multi-dimensional image data may relate to time. For example, a four-dimensional image may comprise a time domain series of three-dimensional images. The image may be acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

The invention is defined in the independent claims. Advantageous yet optional embodiments are defined in the dependent claims.

BRIEF DESCRIPTION OF THE DRAWINGS

These and other aspects of the invention are apparent from and will be elucidated with reference to the embodiments described hereinafter. In the drawings, FIG. 1 shows a system for visualizing a volumetric image of an anatomical structure by generating views of the volumetric image;

FIG. 5 shows a method for visualizing a volumetric image of an anatomical structure by generating views of the volumetric image; and FIG. 6 shows a computer program product comprising instructions for causing a processing system to perform the method.

Figure 2A:
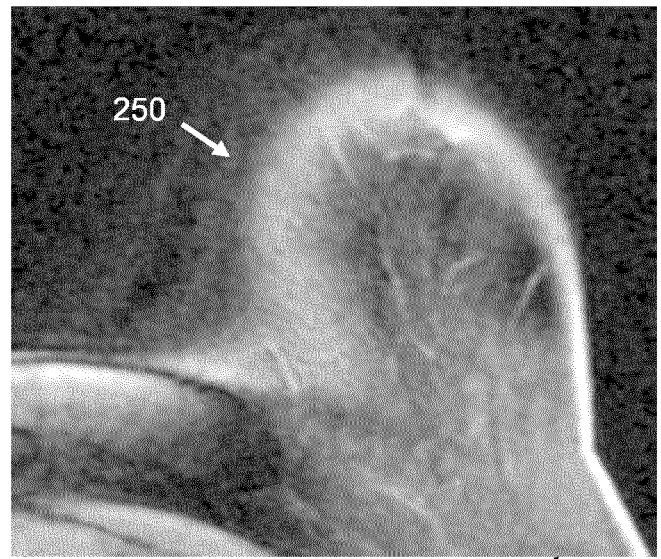
FIG. 2A shows a view of a volumetric breast image, the view representing an axial cross-section through a breast at the bottom of the breast.

It should be noted that items which have the same reference numbers in different Figures, have the same structural features and the same functions, or are the same signals. Where the function and/or structure of such an item has been explained, there is no necessity for repeated explanation thereof in the detailed description.

LIST OF REFERENCE NUMBERS

The following list of reference numbers is provided for facilitating the interpretation of the drawings and shall not be construed as limiting the claims.
020 external storage
022 image data of volumetric image
060 display
080 user input device
082 data provided by user input device
100 system for visualizing a volumetric image
120 image interface
140 display processor
142 output of display processor
160 display output
162 display data
180 user interaction subsystem
182 positioning information
200 view intersecting skin surface of breast at shallow angle
220 view intersecting skin surface of breast at steep angle
250, 252 contour representing skin surface of breast
300 first viewing plane representing first view
310 2D illustration of first viewing plane
312 2D illustration of second viewing plane
320 second viewing plane representing second view
350, 352 surface of anatomical structure
360, 362 local orientation of surface
370 location on surface
400 first view
420 second view
440 onscreen pointer
500 method for visualizing a volumetric image
510 accessing volumetric image
520 generating first view
530 determining local orientation of surface shown in first view
540 generating second view orthogonally intersecting surface
550 generating an outputting display data
600 computer program product
610 instructions

DETAILED DESCRIPTION OF EMBODIMENTS

FIG. 1 shows a system 100 for visualizing a volumetric image of an anatomical structure. The system 100 comprises an image interface 120 for accessing image data 022 of the volumetric image. FIG. 1 shows the system accessing the image data 022 from an external storage 020. Alternatively, the image data 022 may be accessed internally within the system 100, i.e., from an internal storage. The system 100 further comprises a display processor 140. The display processor 140 is shown to access the image data 022 via the image interface 120 from the external storage 020. The system 100 further comprises a display output 160 for generating and outputting display data 162 representing an output of the display processor 140. The display output 160 is shown to provide the display data 162 to a display 060.

The external storage 020 may be a Picture Archiving and Communication System (PACS). The system 100 and the PACS 020 may both be part of a Hospital Information System (HIS). Alternatively, the external storage may take another form.

An operation of the system 100 may be briefly explained as follows. The image interface 120 accesses the image data 022 of the volumetric image. Based on the accessed image data 022, the display processor 140 generates a first view of the volumetric image, with the first view being geometrically defined by a first viewing plane intersecting the volumetric image, and with the first view showing a cross-section of a surface of the anatomical structure. The display processor 140 determines a local orientation of the surface within the volumetric image by analyzing the image data of the volumetric image, the local orientation being determined for at least one location on the surface shown in the first view. Based on the local orientation of the surface, the display processor 140 generates a second view of the volumetric image, the second view being geometrically defined by a second viewing plane intersecting the surface of the anatomical structure in the volumetric image substantially orthogonally at the at least one location on said surface. The display output 160 generates and outputs display data 162 representing an output 142 of the display processor.

It is noted that, instead of a display output 160, the output may be a different type of output in that it may output the data representing the output 142 of the display processor elsewhere, e.g., to an analysis subsystem for further automatic analysis.

FIG. 1 further shows an optional aspect of the system 100, in that the system 100 is shown to comprise a user interaction subsystem 180. The user interaction subsystem 180 is shown to be connected to a user input device 080 such as a mouse, keyboard, touch screen, etc., thereby enabling a user to interact with the system 100 by operating the user input device 080. For example, the user interaction subsystem 180 may enable the user to position an onscreen pointer based on data 082 received from the user input device 080. As such, positioning information 182 may be provided to the display processor 140. Although not shown in FIG. 1, the user interaction subsystem 180 may comprise the display output 160 and a separate user input interface connected to the user input device 080.

It is noted that the operation of the system 100, including various optional aspects thereof, will be explained in more detail with reference to FIGS. 2A-4.

The system 100 may be embodied as, or in, a single device or apparatus, such as a workstation or imaging apparatus. The device or apparatus may comprise one or more microprocessors which execute appropriate software. The software may have been downloaded and/or stored in a corresponding memory, e.g., a volatile memory such as RAM or a non-volatile memory such as Flash. Alternatively, the functional units of the system may be implemented in the device or apparatus in the form of programmable logic, e.g., as a Field-Programmable Gate Array (FPGA). In general, each functional unit of the system may be implemented in the form of a circuit. It is noted that the system 100 may also be implemented in a distributed manner, e.g., involving different devices or apparatuses. For example, the distribution may be in accordance with a client-server model.

FIG. 2A shows a view 200 of a volumetric breast image. The view 200 corresponds to an axial cross-section through a breast at the bottom of the breast. As such, the view 200 may be constituted by an axial slice from a stack of 2D image slices. FIG. 2A serves to illustrate a problem with views showing cross-sections of surfaces of anatomical structure, in that such a surface 250 may be intersected in a shallow manner, i.e., at a shallow angle, which typically leads to the view 200 showing the surface 250 of the anatomical structure in an unclear manner. Here, the term 'shallow' refers to the angle between the viewing plane which geometrically defines the view 200 and the surface 250 of the anatomical structure being substantially smaller than 90 degrees, e.g., 60 degrees or less. As a result, the skin surface 250 of the breast is represented in the view 200 of FIG. 2A by a blurred outline. Such a blurred outline may be difficult to accurately delineate, to accurate interpret, etc.

Figure 2B:
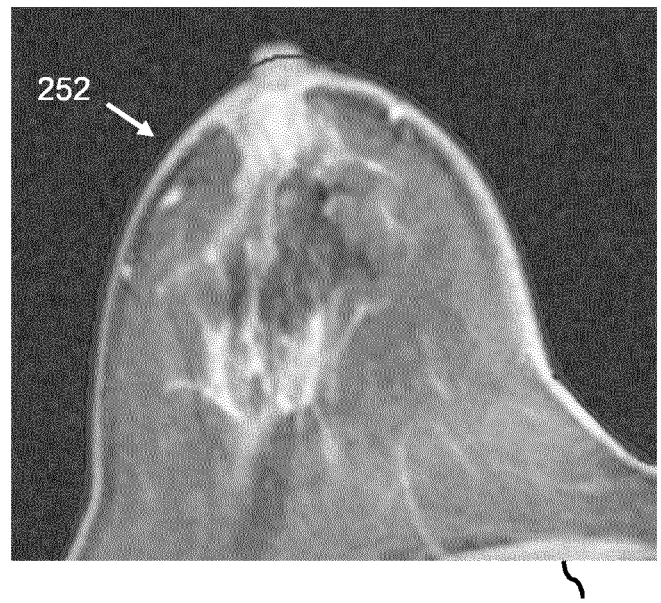
FIG. 2B shows a further view of the volumetric breast image, the further view representing an axial cross-section through the breast at a central slice.

FIG. 2B shows a further view 210 of the volumetric breast image. The further view 210 represents an axial cross-section through the breast at a central slice. Compared to the axial cross-section shown in FIG. 2A, the axial cross-section of FIG. 2B intersects the breast at a steeper, substantially orthogonal angle. As a consequence, the surface 252 of the breast is represented in the view 210 of FIG. 2B by a sharper outline that in FIG. 2A.

The inventors have recognized that, starting from a first view showing a relatively shallow cross-section of a surface of an anatomical structure, a second view may be automatically and purposefully generated which intersects the surface of the anatomical structure in a steeper manner, e.g., orthogonally or substantially orthogonally.

Figure 3A:
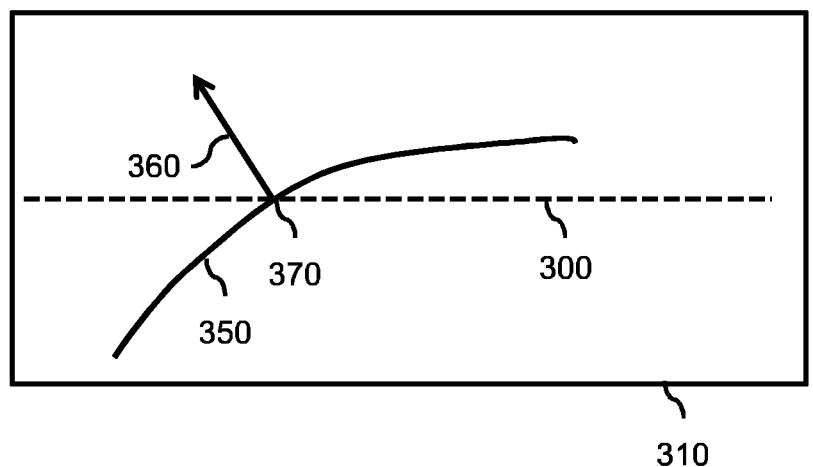
FIG. 3A shows a first viewing plane of a first view intersecting the volumetric image while intersecting a surface of an anatomical structure at a shallow angle.

FIG. 3A schematically shows a first viewing plane 300 of such a first view. For ease of interpretation, FIG. 3A provides a 2D illustration 310 rather than a 3D illustration. As such, the first viewing plane 300 is represented by a line intersecting a surface 350 of an anatomical structure. The first viewing plane 300 may be an image plane representing a currently displayed image. The first viewing plane 300 is shown to intersect the surface 350 of the anatomical structure at a location 370 on the surface. Accordingly, the location 370 is included in the first view as part of the contour representing the surface 350 of the anatomical structure. The first viewing plane 300 intersects the surface 350 of the anatomical structure non-orthogonally, as denoted by an orientation vector 360 representing the orientation of the surface 350 at the location 370 not being contained within the first viewing plane 300.

Figure 3B:
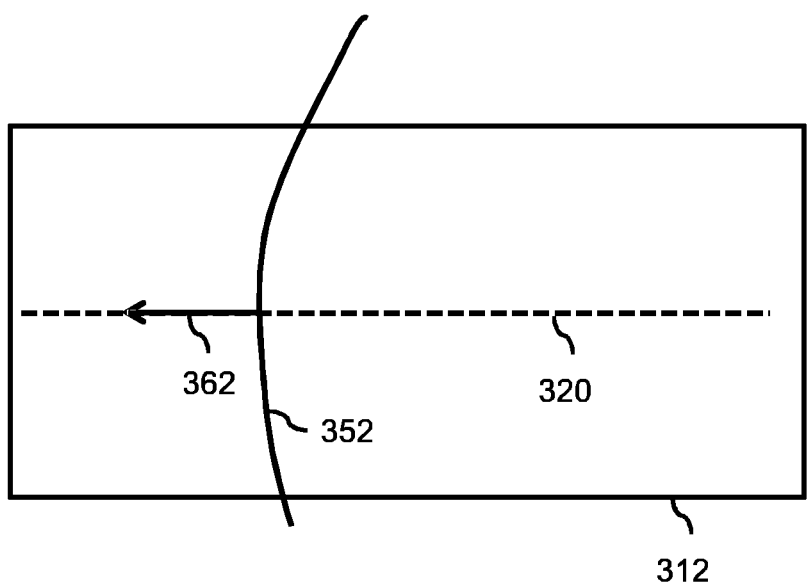
FIG. 3B shows a second viewing plane of a second view intersecting the volumetric image such that the surface of the anatomical structure is intersected orthogonally.

FIG. 3B provides a 2D illustration 312 of a second viewing plane 320. The second viewing plane intersects the surface 352 of the anatomical structure orthogonally. The second viewing plane 320 may be obtained by a rotation of the first viewing plane within the volumetric image. However, for ease of comparison with FIG. 3A, FIG. 3B does not show the second viewing plane being rotated but rather the surrounding image, and as a consequence, the anatomical structure shown therein. As a consequence, the second viewing plane 320 now intersects the surface 352 of the anatomical structure orthogonally, as denoted by the orientation vector 362 being contained within the second viewing plane 320. The above may represent a result of the display processor as claimed, in that the display processor may determine the second viewing plane 320 and subsequently generate the second view.

It is noted that, in general, the display processor may establish the local orientation of the surface within the volumetric image as an orientation vector pointing in a direction of the steepest change in image intensity from the at least one location on the surface of the anatomical structure. The display processor may determine the direction of the steepest change in the image intensity by applying an image filter to the image data. For example, the display processor may apply a Hessian filter to the image data. Hessian filters are well known within the fields of image processing and image analysis. Alternatively, any other suitable detection technique may be used to determine the direction of the steepest change in image intensity within the image data. Having determined the orientation vector, the display processor may determine the second viewing plane by rotating the first viewing plane so as to contain the orientation vector. To minimize and/or avoid so-termed in-plane rotation of the content of the second view with respect to the first view, the display processor may use a rotation transformation about a smallest absolute rotation angle. Namely, out of all possible rotation transformations transforming the first viewing plane into the second viewing plane, e.g., along various different axes, a particular rotation transformation may be selected, namely a rotation transformation about the smallest absolute rotation angle.

Figure 4:
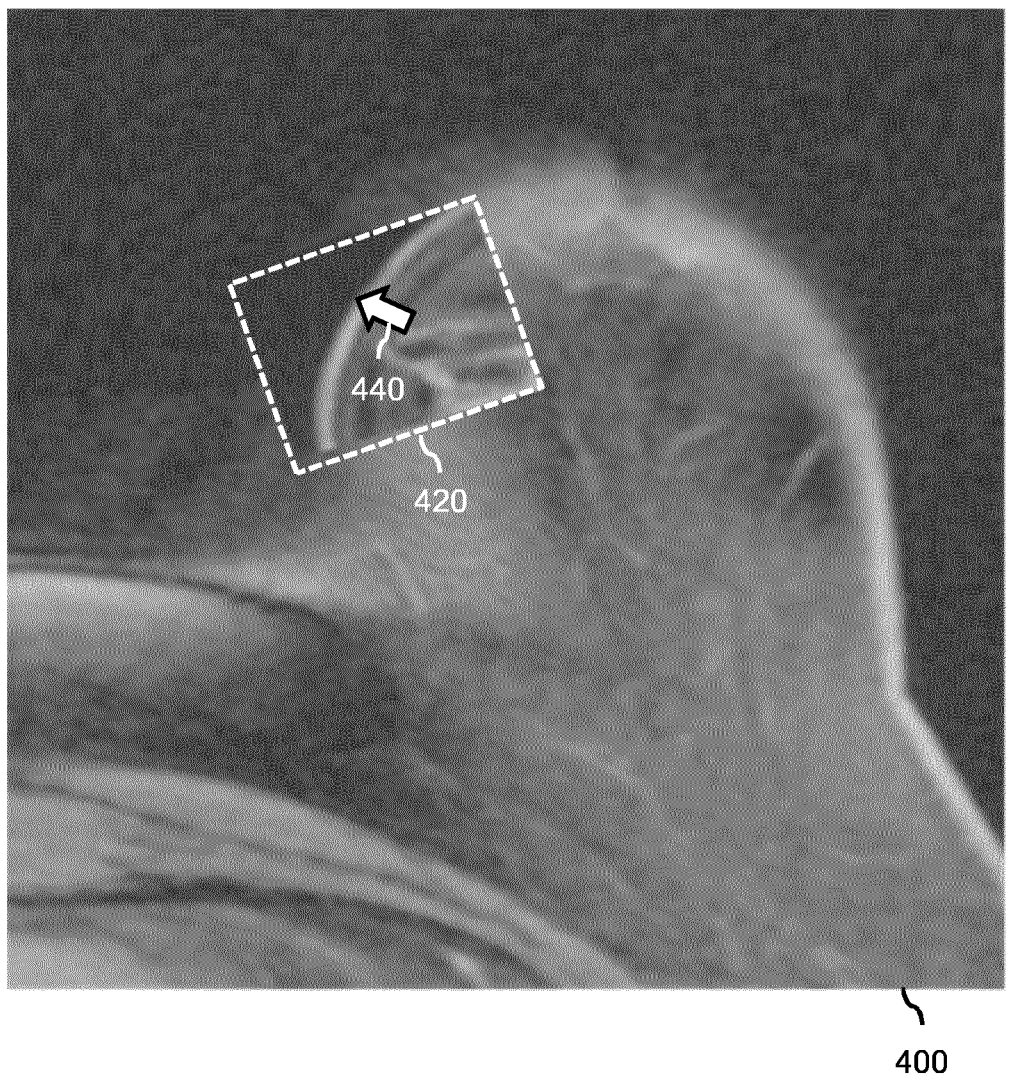
FIG. 4 shows the second view being displayed as a local overlay overlaying the first view at a position of an onscreen pointer.

FIG. 4 shows the second view 420 being displayed as a local overlay overlaying the first view 400 at a position of an onscreen pointer 440. This figure relates to the following. A user may be enabled to position an onscreen pointer 440, e.g., by operating a user input device connected to the user interaction subsystem of the system 100 of FIG. 1. For example, the onscreen pointer 440 may be provided for use in a graphical user interface established by the user interaction subsystem. The display processor may be configured for determining the at least one location on the surface based on a position of the onscreen pointer 440. For example, the location may be represented by a current position of the onscreen pointer 440, or by a location on the surface of the anatomical structure which is nearest to the current position. The display processor may generate the second view 420 as a local overlay over part of the first view 400, thereby replacing the first view in a neighborhood of the position of the onscreen pointer 440. For example, the overlay may provide a continuous, real-time view showing the surface of the anatomical structure being orthogonally intersected as the use moves the onscreen pointer 440 over the first view 400. The second view 420 may be generated based on a volume of interest. The volume of interest may represent the neighborhood in that it may include the current position of the onscreen pointer and its surroundings in the volumetric image. The volume of interest may have a cubical or a spherical shape, but other shapes are equally conceivable. For example, the shape may be adapted to the shape of the anatomical structure. The volume of interest may constitute input to a multi-planar reformatting technique. As such, the multi-planar reformatting may be applied to the volume of interest rather than the entire volumetric image.

Although not shown in FIG. 4, the display processor may blend the second view with the first view at a boundary of the volume of interest so as to establish a gradual transition between the overlay of the second view and the first view. It is noted that the second view may also be displayed in various other ways. For example, the second view may be provided in a separate window which adjoins a window showing the first view, e.g., in a side-by-side configuration. The second view may also entirely replace the first view. The second view may also be provided only upon selecting a delineation mode in a graphical user interface. Having selected to the delineation mode, the user interaction subsystem may enable the user to delineate the surface of the anatomical structure in the second view.

FIG. 5 shows a method 500 for visualizing a volumetric image of an anatomical structure by generating views of the volumetric image. The method 500 may correspond to an operation of the system 100 of FIG. 1. However, this is not a limitation, in that the method 500 may also be performed in separation of the system 100.

The method 500 comprises, in an operation titled "ACCESSING VOLUMETRIC IMAGE", accessing 510 image data of the volumetric image. The method 500 further comprises, in an operation titled "GENERATING FIRST VIEW", generating 520 a first view of the volumetric image, the first view being geometrically defined by a first viewing plane intersecting the volumetric image, the first view showing a cross-section of a surface of the anatomical structure. The method 500 further comprises, in an operation titled "DETERMINING LOCAL ORIENTATION OF SURFACE SHOWN IN FIRST VIEW", determining 530 a local orientation of the surface within the volumetric image by analyzing the image data of the volumetric image, the local orientation being determined for at least one location on the surface shown in the first view. The method 500 further comprises, in an operation titled "GENERATING SECOND VIEW ORTHOGONALLY INTERSECTING SURFACE", based on the local orientation of the surface, generating 540 a second view of the volumetric image, the second view being geometrically defined by a second viewing plane intersecting the surface of the anatomical structure in the volumetric image orthogonally at the at least one location on said surface. The method 500 further comprises, in an operation titled "GENERATING AND OUTPUTTING DISPLAY DATA", generating and outputting 550 display data representing an output of the display processor.

It will be appreciated that the above operation may be performed in any suitable order, e.g., consecutively, simultaneously, or a combination thereof, subject to, where applicable, a particular order being necessitated, e.g., by input/output relations. For example, the second view may be generated conditionally when switching a graphical user interface to a particular mode such as a delineation mode. The second view may also be generated repeatedly for different locations on the surface shown in the first view, e.g., as indicated by a position of an onscreen pointer. Here, the first view may represent a navigational view, e.g., for enabling the user to navigate through the volumetric image.

The method 500 may be implemented on a computer as a computer implemented method, as dedicated hardware, or as a combination of both. As also illustrated in FIG. 6, instructions for the computer, e.g., executable code, may be stored on a computer readable medium 600, e.g., in the form of a series 610 of machine readable physical marks and/or as a series of elements having different electrical, e.g., magnetic, or optical properties or values. The executable code may be stored in a transitory or non-transitory manner. Examples of computer readable mediums include memory devices, optical storage devices 600, integrated circuits, servers, online software, etc. FIG. 6 shows an optical disc.

It will be appreciated that the invention as claimed may be advantageously used in the following use-cases. In many clinical applications involving volumetric medical image data such as MR, CT, or 3D ultrasound images, a user may have to manually define or correct a predefined outline of a 3D sub-volume, e.g., a tumor or an organ. Radiologists usually inspect volumetric images by looking at 2D cross-sections through the data, either along the orientations of the underlying voxel grid (e.g., axial, coronal, and sagittal) or oblique slices. Outlining of 3D objects can be performed by drawing closed contours in adjacent 2D slices and subsequently combining the stack of closed contours into a 3D surface mesh. The invention as claimed may be advantageously used to detect the local orientation of a surface in a volumetric image at the current location of the mouse pointer. In a reformatting step, a local volume of interest around the mouse pointer may be reoriented such that the detected surface cuts orthogonally through the image slice. That way the contour to be traced may be apparently sharpened. For that purpose, at any given position of the mouse pointer over the image, a filter, e.g., a Hessian filter, or a 3D gradient may be applied to analyze the local orientation of the imaged structure. The local orientation may be represented by a vector O pointing into the direction of the steepest change in image intensity. A plane P may be defined which is 1) orthogonal to the image plane (e.g., the viewing plane defining the currently displayed view) and 2) contains the orientation vector. Here, the plane P may be used to select the rotation with the smallest possible rotation angle which brings the orientation vector into the viewing plane. The rotation axis may be normal to the plane P. All other rotations about other axes may be associated with larger angles. A set of voxels around the mouse pointer position may be defined as the Volume of Interest (VOI) for the given application. The VOI may be cube-shaped or spherical or take a more general shape. The size may be pre-defined, application specific, or user-defined. A rotation may be applied to the VOI relocating the voxels to new locations. The rotation may be defined such that the axis of the rotation is contained in the viewing plane and orthogonal to the plane P. The angle of the rotation may be defined as the smallest angle (absolute value) that maps the orientation vector O into the image plane. This way the image appearance may be improved with the minimal possible angulation of the image volume. This way the local image structure in the VOI may be presented in such a way that the cross section of the surface is presented in a clearer manner and easily traceable by the user. The rotation transformation R may also only applied at the mouse pointer position itself and fade out towards the boundaries of the VOI by applying a weighted transformation wR, where w drops from 1 at the center of the VOI to 0 at the VOI boundary. This may avoid the discontinuous transitions at the VOI boundary.

It is noted that while the above examples refer to the anatomical structure being a breast, the invention as claimed may be advantageously used to obtain a view of other anatomical structures as well so as to show their surface in a clearer manner.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be subdivided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for visualizing a volumetric image of an anatomical structure, the system comprising:
    an image interface for accessing image data of the volumetric image;
    a display processor configured for:
        i) generating a first view of the volumetric image, the first view being geometrically defined by a first viewing plane intersecting the volumetric image, the first view showing a cross-section of a surface of the anatomical structure,
        ii) determining at least one location on the surface based on a position of an onscreen pointer;
        iii) determining a local orientation of the surface within the volumetric image by analyzing the image data of the volumetric image, the local orientation being determined for the at least one location on the surface shown in the first view, and
        iv) based on the local orientation being determined for the at least one location on the surface, generating a second view of the volumetric image, the second view being geometrically defined by a second viewing plane intersecting the surface of the anatomical structure in the volumetric image substantially orthogonally at the at least one location on said surface;
    a display output for generating and outputting display data, the display data representing an output of the display processor; and
    a user interaction subsystem for enabling a user to position an onscreen pointer over the first view,
    wherein the display processor is configured for determining the at least one location on the surface based on a position of the onscreen pointer.

2. The system according to claim 1, wherein the user interaction subsystem is configured for enabling the user to delineate the surface of the anatomical structure in the second view.

3. The system according to claim 1, wherein the display processor is configured for:
    determining a volume of interest in the volumetric image which includes the at least one location on the surface; and
    generating the second view based on the volume of interest.

4. The system according to claim 3, wherein the volume of interest has a cubical or a spherical shape.

5. The system according to claim 1, wherein the display processor is configured for generating the second view as an overlay over part of the first view.

6. The system according to claim 5, wherein the part of the first view being overlaid corresponds to the volume of interest.

7. The system according to claim 6, wherein the display processor is configured for blending the second view with the first view at a boundary of the volume of interest so as to establish a gradual transition between the overlay of the second view and the first view.

8. The system according to claim 1, wherein the display processor is configured for establishing the local orientation of the surface within the volumetric image as an orientation vector pointing in a direction of the steepest change in image intensity from the at least one location on the surface of the anatomical structure.

9. The system according to claim 8, wherein the display processor is configured for determining the second viewing plane by rotating the first viewing plane so as to contain the orientation vector with a rotation transformation about a smallest absolute rotation angle.

10. The system according to claim 8, wherein the display processor is configured for determining the direction of the steepest change in the image intensity by applying an image filter to the image data.

11. The system according to claim 10, wherein the image filter is a Hessian filter.

12. A workstation or imaging apparatus comprising the system according to claim 1.

13. A method for visualizing a volumetric image of an anatomical structure, the method comprising:
    accessing image data of the volumetric image;
    generating a first view of the volumetric image, the first view being geometrically defined by a first viewing plane intersecting the volumetric image, the first view showing a cross-section of a surface of the anatomical structure;
    determining at least one location on the surface based on a position of an onscreen pointer and a local orientation of the surface within the volumetric image by analyzing the image data of the volumetric image, the local orientation being determined for the at least one location on the surface shown in the first view;

based on the local orientation being determined for the at least one location on the surface, generating a second view of the volumetric image, the second view being geometrically defined by a second viewing plane intersecting the surface of the anatomical structure in the volumetric image substantially orthogonally at the at least one location on said surface;

generating and outputting display data, the display data representing an output of the display processor;

enabling a user to position an onscreen pointer over the first view; and determining the at least one location on the surface based on a position of the onscreen pointer.

14. A non-transitory computer-readable medium comprising instructions for causing a processor system to perform the method according to claim 13.

* * * * *